United States Patent
An et al.

(10) Patent No.: US 11,892,440 B2
(45) Date of Patent: Feb. 6, 2024

(54) **METHOD FOR EVALUATING COLD TOLERANCE OF *HEVEA BRASILIENSIS***

(71) Applicant: Rubber Research Institute, Chinese Academy of Tropical Agricultural Sciences, Haikou (CN)

(72) Inventors: Zewei An, Haikou (CN); Yanshi Hu, Haikou (CN); Xia Zeng, Haikou (CN); Zhi Deng, Haikou (CN); Wenguan Wu, Haikou (CN); Han Cheng, Haikou (CN); Jialin Fang, Haikou (CN)

(73) Assignee: RUBBER RESEARCH INSTITUTE, CHINESE ACADEMY OF TROPICAL AGRICULTURAL SCIENCES, Haikou (CN)

( * ) Notice: Subject to any disclaimer, the term of this patent is extended or adjusted under 35 U.S.C. 154(b) by 0 days.

(21) Appl. No.: 18/332,018

(22) Filed: Jun. 9, 2023

(65) Prior Publication Data
US 2023/0400443 A1 Dec. 14, 2023

(30) Foreign Application Priority Data

Jun. 13, 2022 (CN) .......................... 202210659899.2

(51) Int. Cl.
*G01N 33/00* (2006.01)
*G06N 5/048* (2023.01)

(52) U.S. Cl.
CPC ......... *G01N 33/0098* (2013.01); *G06N 5/048* (2013.01)

(58) Field of Classification Search
CPC ................................................ G01N 33/0098
See application file for complete search history.

(56) References Cited

FOREIGN PATENT DOCUMENTS

| CN | 103712921 A | * | 4/2014 |
| CN | 105830842 A | | 8/2016 |
| CN | 106248739 A | | 12/2016 |

(Continued)

OTHER PUBLICATIONS

CN-112674123-A—translate (Year: 2021).*

(Continued)

*Primary Examiner* — Kristina M Deherrera
*Assistant Examiner* — Fatemeh Esfandiari Nia
(74) *Attorney, Agent, or Firm* — Rachel Pilloff; Sean Passino; Martin Cosenza (57) ABSTRACT

A method for evaluating cold tolerance of *Hevea brasiliensis* includes: (1) taking different one-year-old germplasm plants of the *Hevea brasiliensis* with second whorls of leaves entering a stable period as materials, firstly culturing the materials at a normal temperature, then treating the materials at a low temperature, and finally respectively measuring relative electrical conductivities of the materials cultured at the normal temperature and physiological indexes of the cold tolerance of the materials treated at the low temperature, where a variety 93114 is used as a cold tolerance control and a Reyan 73397 is used as a sensitive control; and (2) according to changes of the physiological indexes of the cold tolerance in the germplasm plants of the *Hevea brasiliensis*, comprehensively evaluating the cold tolerance of the materials by using a fuzzy membership function method. When comprehensive indexes of the cold tolerance are larger, the cold tolerance of the materials is better.

3 Claims, 4 Drawing Sheets (56) References Cited

FOREIGN PATENT DOCUMENTS

| CN | 111961680 A | * | 11/2020 | ......... C12N 15/8273 |
|----|-------------|---|---------|------------------------|
| CN | 112674123 A | * | 4/2021  |                        |
| CN | 112778408 A | * | 5/2021  | ........... C07K 14/415 |
| CN | 112816426 A | * | 5/2021  |                        |
| CN | 112816426 A |   | 5/2021  |                        |
| KR | 101531793 B1 |  | 6/2015  |                        |

OTHER PUBLICATIONS

CN-103712921-A—Translate (Year: 2014).*
CN-111961680-A—English (Year: 2020).*
CN-112816426-A—English (Year: 2021).*
CN-112778408-A—English (Year: 2021).*
Hu et al.Comprehensive evaluation of cold tolerance of new amazon HEVEA germplasm (2012) 15-0051-05 China Academic Journal Electronic Publishing House. (Year: 2012).*
Hu et al. "Comprehensive evaluation of cold tolelance of new amazon HEVEA germplasm" (2012) 15-0051-05 China Academic Journal Electronic Publishing House.

* cited by examiner

METHOD FOR EVALUATING COLD TOLERANCE OF HEVEA BRASILIENSIS

CROSS-REFERENCE TO RELATED APPLICATIONS

This application claims priority of Chinese Patent Application No. 202210659899.2, filed on Jun. 13, 2022, the entire contents of which are incorporated herein by reference.

TECHNICAL FIELD

The application relates to the field of forestry production, and in particular to a method for evaluating cold tolerance of *Hevea brasiliensis*.

BACKGROUND

*Hevea brasiliensis* is a typical tropical cash crop. The place between 10° S and 15° N is universally recognized as the most favorable place to grow *Hevea brasiliensis*, where the annual average temperature is 25 degree Celsius (° C.) to 27° C. The *Hevea brasiliensis* planting area in China is ranged from 18° N to 24° N, which is the northernmost area for *Hevea brasiliensis* planting in the world, *Hevea brasiliensis* trees here have an annual average temperature of 19° C. to 23° C., often suffer low-temperature cold damage below 10° C., and may only be found in Hainan Province, southern Yunnan Province and Zhanjiang, Guangdong Province. At present, the contradiction between supply and demand of natural rubber in China becomes increasingly sharp, and the self-sufficiency rate of the natural rubber is less than 20 percent (%) because of the potential of limited increase in yield per unit area and the serious restriction from low temperatures. Low-temperature stress has become the main bottleneck restricting the development of natural rubber industry in China, and it is particularly important to cultivate cold-tolerant *Hevea brasiliensis* varieties in China.

In the process of breeding, it is helpful to accurately evaluate cold tolerance of breeding materials at the seedling stage is to correctly select materials with cold tolerance, shorten the breeding period and accelerate the breeding process. At present, there are two main methods to evaluate the cold tolerance of *Hevea brasiliensis*: one is to carry out field survey on the plants suffering low-temperature cold injury in the natural environment, and grade damage degrees of the plants according to their symptoms, so as to evaluate their cold tolerance (NY/T 221-2016 Technical Regulations for Cultivation of *Hevea brasiliensis*); the other is to artificially simulate the low-temperature cold damage indoor, and treat the ex vivo shoots of one- to two-year-old seedlings at 10° C., 0° C. and −1° C. respectively, and then grade their cold damage according to the damage degrees, so as to evaluate the cold tolerance of the materials (NYT 1314-2007 Technical Code for Evaluating Germplasm Resources—*Hevea brasiliensis*). The two evaluation methods of cold tolerance above are based on the symptoms after cold damage, and the first method is to evaluate the cold tolerance in the natural environment, and the second method is to evaluate the cold tolerance using ex vivo materials. Since the cold tolerance of plants is a comprehensive expression of intrinsic many factors and the cold tolerance shown by ex vivo materials is quite different from that of in vivo materials, the ex vivo materials cannot accurately reflect the true cold tolerance of plants. Therefore, it is urgent to develop a method for evaluating cold tolerance of *Hevea brasiliensis* that is not limited by the natural environment and may accurately reflect the cold tolerance of *Hevea brasiliensis*.

SUMMARY

An objective of the application is to provide a method for evaluating cold tolerance of *Hevea brasiliensis*, so as to solve problems existing in the prior art. The method may not only accurately evaluate the cold tolerance of materials, but also evaluate the cold tolerance of the materials at a seedling stage without being limited by natural climatic environment.

To achieve the above objective, the present application adopts a following technical scheme.

A method for evaluating cold tolerance of *Hevea brasiliensis* includes:

(1) taking different one-year-old germplasm plants of the *Hevea brasiliensis* with second whorls of leaves entering a stable period as materials, firstly culturing the materials at a normal temperature, then treating the materials at a low temperature, and respectively measuring relative electrical conductivities of the materials cultured at the normal temperature and physiological indexes of the cold tolerance of the materials treated at the low temperature, where a variety 93114 is used as a cold tolerance control and a Reyan 73397 is used as a sensitive control; and (2) according to changes of the physiological indexes of the cold tolerance in the germplasm plants of the *Hevea brasiliensis*, comprehensively evaluating the cold tolerance of the materials by using a fuzzy membership function method.

When comprehensive indexes of the cold tolerance are larger, the cold tolerance of the materials is better; materials with comprehensive indexes of the cold tolerance larger than or equal to a comprehensive index of the variety 93114 as the cold tolerance control have strong cold tolerance, materials with comprehensive indexes smaller than or equal to a comprehensive index of the Reyan 73397 as the sensitive control have low cold tolerance, and materials with comprehensive indexes between the comprehensive index of the variety 93114 as the cold tolerance control and the comprehensive index of the Reyan 73397 as the sensitive control have medium cold tolerance.

In an embodiment, a membership function formula is $Uij=(Xij-Xjmin)/(Xjmax-Xjmin)$.

In an embodiment, if the physiological indexes of the cold tolerance are negatively related to the cold tolerance, an inverse function is used for conversion, where inverse function value=$1-(Xij-Xjmin)/(Xjmax-Xjmin)$; the comprehensive indexes of the cold tolerance are $$Ui = \sum_{j=1}^{n} Uij/n,$$

where i is an i-th material of all the materials to be tested, j is a j-th physiological index of the cold tolerance of all measured indexes, Xij is a measured value of a j-th physiological index of the i-th material, Xjmin and Xjmax are a minimum measured value and a maximum measured value of j indexes of all the materials to be tested respectively, Ui is a comprehensive index of the cold tolerance of the i-th material, and n is a number of the measured physiological indexes of the cold tolerance.

In an embodiment, the treating at the low temperature specifically includes: culturing the different germplasm plants of the *Hevea brasiliensis* to be tested at a normal temperature of 26° C. for 48 hours (h), and then treating at 0° C. for 72 h, where a humidity is kept at 90% and a photoperiod includes 16 h of daylight/8 h of darkness.

In an embodiment, the physiological indexes of the cold tolerance include chlorophyll contents, soluble sugar contents, malondialdehyde contents, proline contents, the relative electrical conductivities and injury rates.

The application also provides an application of the method in genetic breeding of the *Hevea brasiliensis*.

The embodiments of the present application have following effects.

In the application, living seedlings are treated at low temperature, and the cold tolerance of the materials is evaluated according to the changes of the physiological indexes of the cold tolerance in the plants. The method disclosed in the application may not only accurately evaluate the cold tolerance of the materials, but also evaluate the cold tolerance of the materials at the seedling stage without being limited by the natural climatic environment. The evaluation method provides a scientific basis for rapid breeding of a *Hevea brasiliensis* variety with the cold tolerance.

BRIEF DESCRIPTION OF THE DRAWINGS

In order to more clearly explain the embodiments of the present application or the technical solutions in the prior art, the following will briefly introduce the drawings that need to be used in the embodiments. Obviously, the drawings in the following description are only some embodiments of the present application. For those of ordinary skill in the art, other drawings may be obtained according to these drawings without any creative effort.

DETAILED DESCRIPTION

Various exemplary embodiments of the present application are now described in detail, and this detailed description should not be considered as a limitation of the present application, but should be understood as a more detailed description of some aspects, characteristics and embodiments of the present application.

It should be understood that the terminology described in the application is only for describing specific embodiments and is not used to limit the application. In addition, for the numerical range in this application, it should be understood that each intermediate value between the upper limit and the lower limit of the range is also specifically disclosed. The intermediate value within any stated value or stated range and each smaller range between any other stated value or intermediate value within the stated range are also included in this application. The upper and lower limits of these smaller ranges can be independently included or excluded from the range.

Unless otherwise specified, all technical and scientific terms used herein have the same meaning as commonly understood by one of ordinary skill in the art described in the application. Although the application only describes the preferred methods and materials, any methods and materials similar or equivalent to those described herein may also be used in the implementation or testing of the application.

It is obvious to those skilled in the art that many improvements and changes may be made to the specific embodiments of the specification of the application without departing from the scope or spirit of the application. Other implementation methods obtained from the specification of the application are obvious to the skilled person. The specification and embodiments of the application are only exemplary.

The terms "comprising", "including", "having" and "containing" used in the application are all open terms, which means including but not limited to.

The following embodiments relate to germplasm resources of *Hevea brasiliensis*, and all of the germplasm resources of the *Hevea brasiliensis* are taken from the National Rubber Tree Germplasm Repository.

Embodiment 1: a method for evaluating the cold tolerance of the *Hevea brasiliensis*

Figure 1:
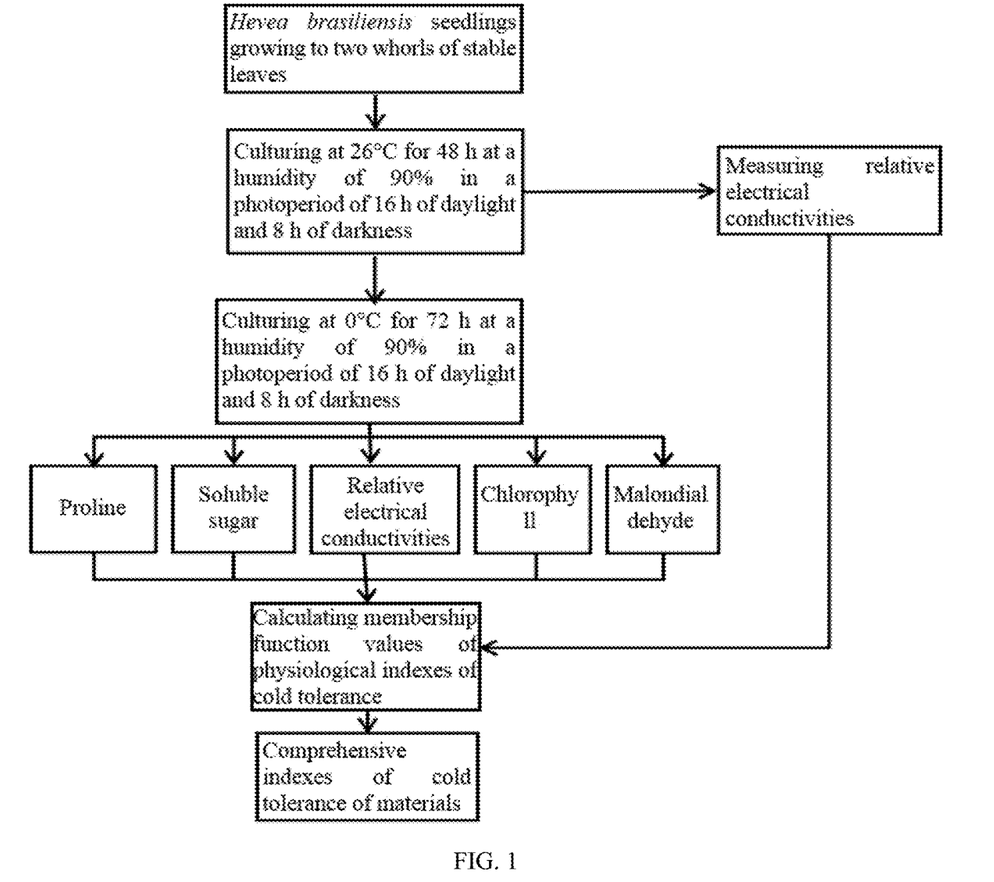
FIG. 1 is a flow chart of a method for evaluating cold tolerance of seedlings of *Hevea brasiliensis*.

The embodiment is described in more detail from selecting materials to evaluating the cold tolerance (a flow chart of the evaluation method is shown in FIG. 1).

1. Materials Preparation

Sixteen germplasm materials of the *Hevea brasiliensis* are provided, where all of the germplasm materials are plants budded in the same year with second whorls of leaves entering a stable period, a variety named 93114 is selected as a cold tolerance control, and Reyan 73397 is selected as a sensitive control, where each of the materials is provided in 3 replicates.

2. Low Temperature Treatment Conditions

Figure 2:
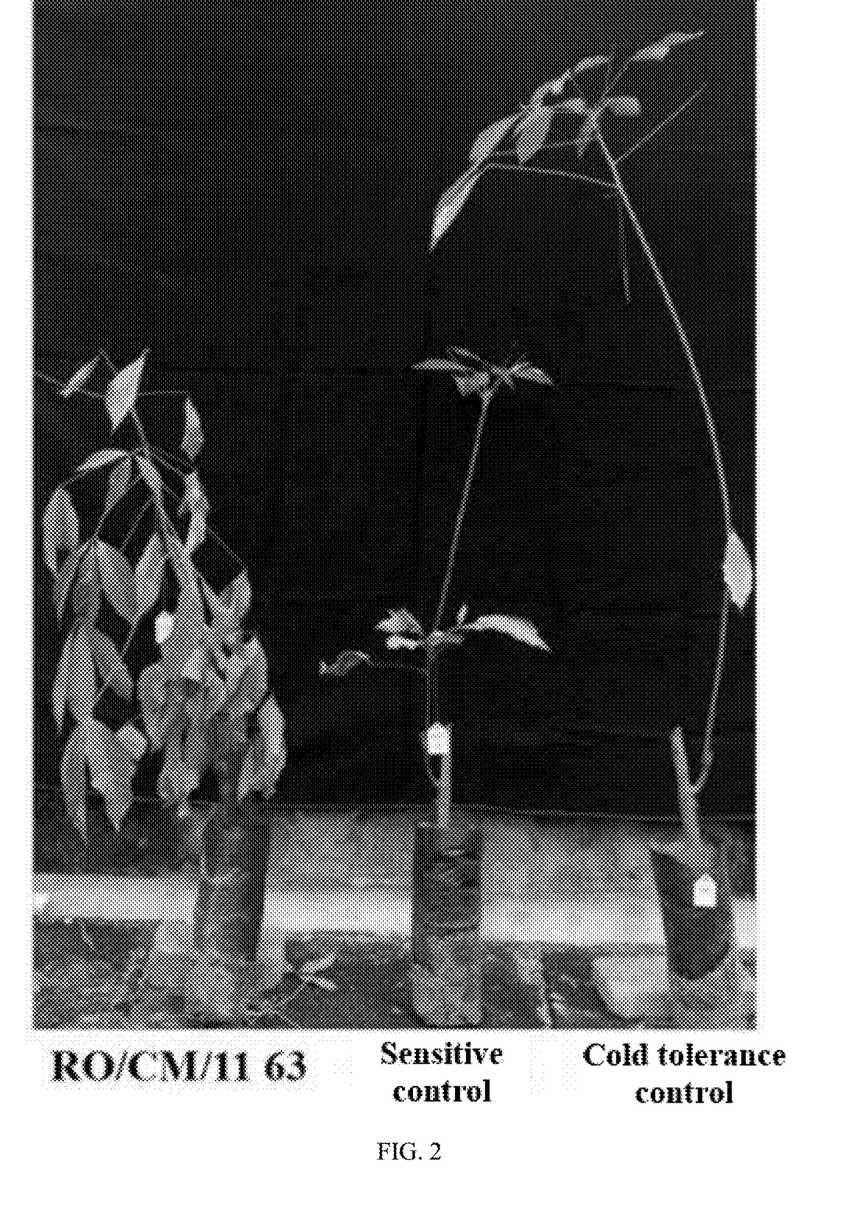
FIG. 2 shows phenotypes of germplasm materials of *Hevea brasiliensis* RO/CM/11 63, a Reyan 73397 as a sensitive control and a variety 93114 as a cold tolerance control after low temperature treatment for 72 h.
Figure 3:
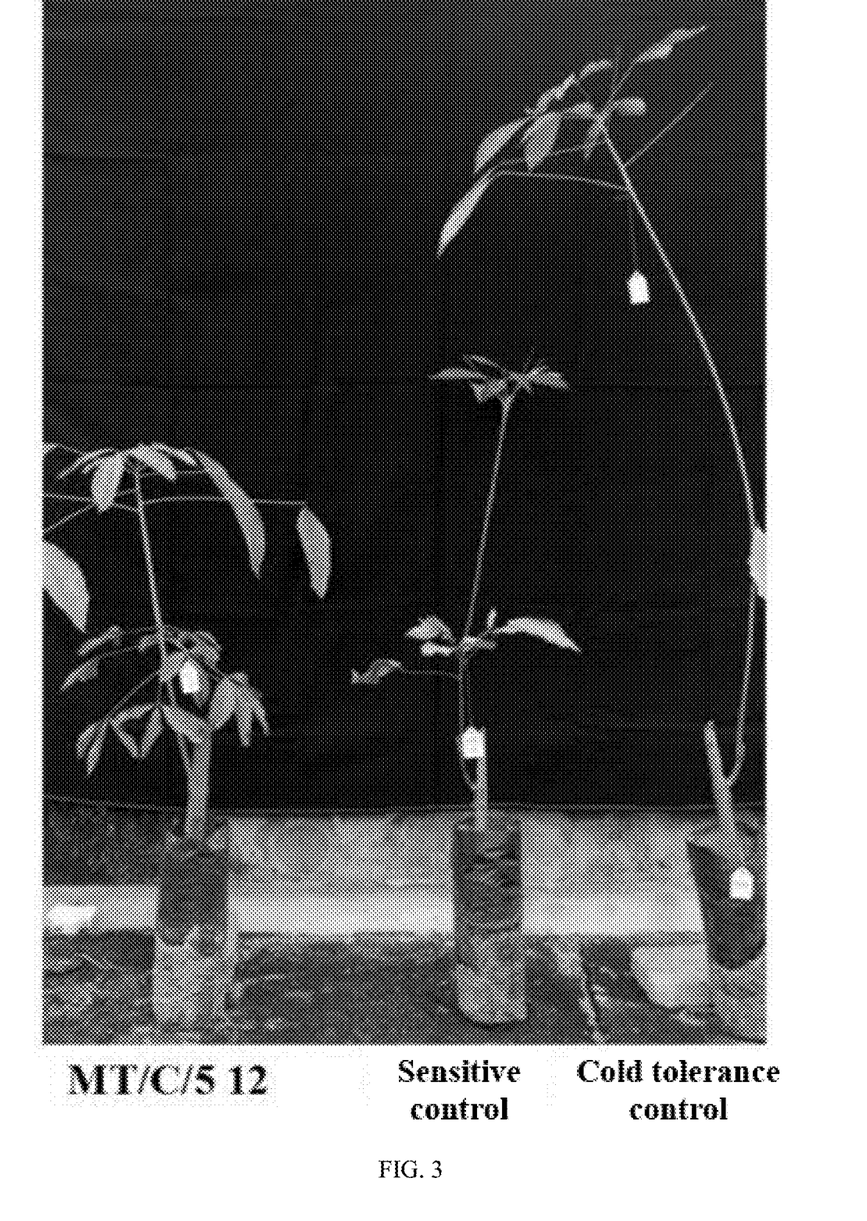
FIG. 3 shows phenotypes of germplasm materials of *Hevea brasiliensis* MT/C/5 12, a Reyan 73397 as a sensitive control and a variety 93114 as a cold tolerance control after low temperature treatment for 72 h.
Figure 4:
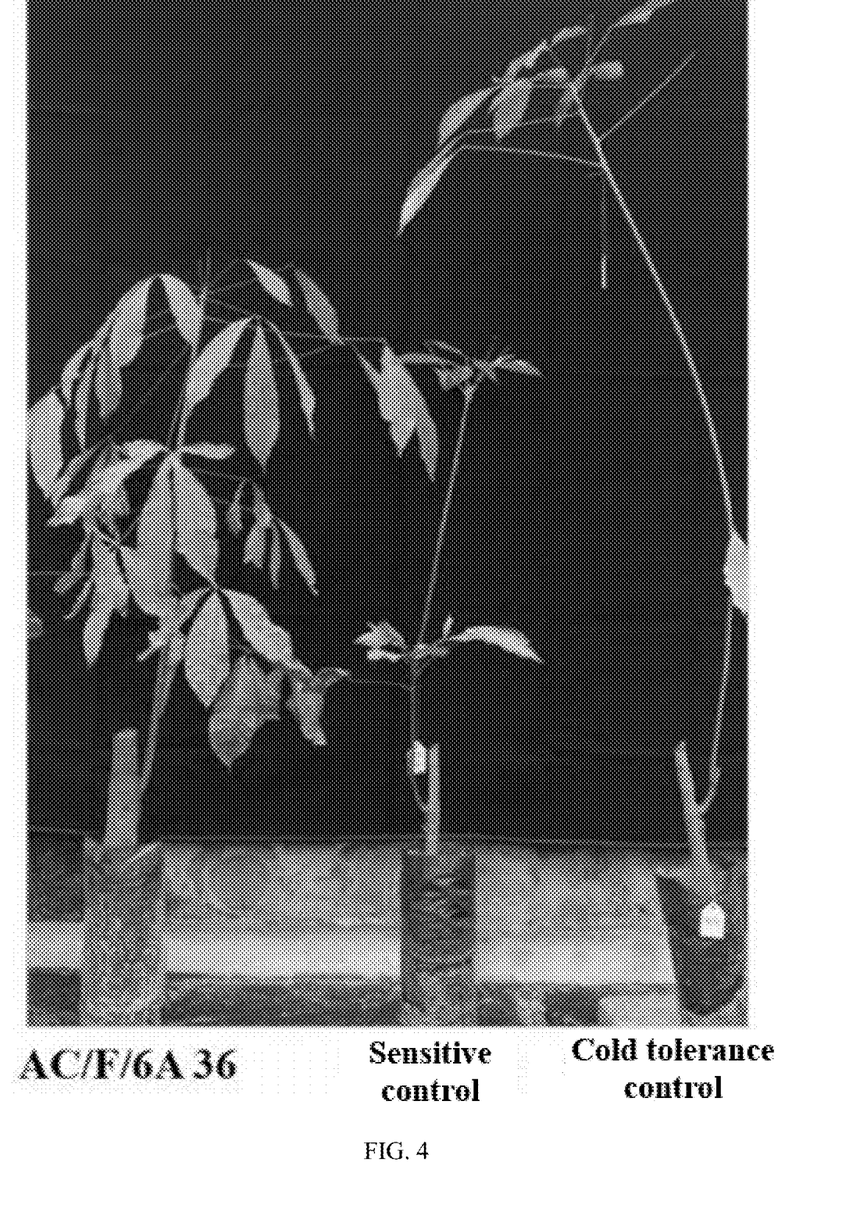
FIG. 4 shows phenotypes of germplasm materials of *Hevea brasiliensis* AC/F/6A 36, a Reyan 73397 as a sensitive control and a variety 93114 as a cold tolerance control after low temperature treatment for 72 h.

The materials to be evaluated are treated in an artificial climate chamber under following conditions: culturing the materials for 48 h at 26° C., for 72 h at 0° C., under a humidity of 90%, 16 h of daylight and 8 h of darkness. Phenotypes of the germplasm materials of the *Hevea brasiliensis* AC/F/6A 36, MT/C/5 12 and RO/CM/11 63, the Reyan 73397 as the sensitive control and the variety 93114 as the cold tolerance control after the above low temperature treatment are shown in FIG. 2-FIG. 4.

3. Determination of Physiological Indexes of the Cold Tolerance

Six leaves from each of the materials are taken as samples for the determination of soluble sugar, malondialdehyde, proline and relative electrical conductivities.

Determination of the chlorophyll contents: selecting three leaves from each of the materials, fixing three areas to be determined on each of the leaves, determining each of the areas three times with a portable chlorophyll analyzer CCM200 plus, and taking an average value of obtained chlorophyll contents of the three leaves as a chlorophyll content in each of the materials.

Determination of the soluble sugar: determining the soluble sugar in the samples with a soluble sugar detection kit by a micro-determination method, where all operations are carried out according to instructions of the soluble sugar detection kit; calculating sample concentrations y (milligram per milliliter (mg/mL)) according to a standard curve; and calculating soluble sugar contents in the samples by a following formula: soluble sugar (mg/g fresh weight)=(y×V1)÷(W×V1÷V2)=10×y÷ W, where V1: a volume of the added samples, 0.2 mL; V2:a volume of extracts, 10 mL; W: a fresh weight of the samples, gram (g).

Determination of the malondialdehyde: determining the malondialdehyde in the samples with a malondialdehyde detection kit by the micro-determination method, where all operations are carried out according to the instructions of the malondialdehyde detection kit; and calculating malondialdehyde contents of the samples by a following formula: malondialdehyde content (nanomole per gram (nmol/g) fresh weight)=[6.45×(A532−A600)−0.56×A450]×$V_{total}$÷(W×$V_{sample}$÷$V_{extract}$)=5×[6.45×(A532−A600)−0.56×A450]÷W, where $V_{total}$: a total volume of a reaction system, 1 mL; $V_{sample}$: V1: a volume of the added samples, 0.2 mL. W: a fresh weight of the samples, g; $V_{extract}$: a volume of extracts, 1 mL.

Determination of the proline: determining the proline in the samples with a proline detection kit by the micro-determination method, where all operations are carried out according to the instructions of the proline detection kit, and calculating sample concentrations y (mg/mL) by a following formula according to a standard curve: proline (microgram per gram (μg/g) fresh weight)=(y×V1)÷(W×V1÷V2)=y÷W, V1: a volume of the added samples; V2: a volume of extracts, 1 mL; W: a fresh weight of the samples, g.

Determination of the relative electrical conductivities: beating the samples into leaf disks with a diameter of 0.6 millimeter (mm), weighing 0.5 g of the leaf disks, putting the leaf disks into a 15 mL centrifugal tube, adding 10 mL of ultrapure water, shaking and soaking the centrifugal tube by a shaker for 24 h, measuring electrical conductivities of the leaves with a SevenEasy conductivity meter to represent electrolyte leakages after the low temperature treatment, then putting the leaf disks into a water bath pot for boiling water bath for 30 minutes (min), cooling to the normal temperature, measuring electrical conductivities of the leaves to represent total electrolyte leakages, and taking the relative electrical conductivities and injury rates to represent electrolyte leakage rates, where a calculation formula is as follows: relative electrical conductivity=(T1÷T2)×100%, and injury rate=(T1/T2−C1/C2)÷(1−C1/C2)×100%, where C1 is electrical conductivities of the control leaves, C2 is electrical conductivities of the control leaves after the water bath; T1 is electrical conductivities of sample leaves after low temperature treatment, and T2 is electrical conductivities of the leaves after the water bath.

4. Evaluation of the Cold Tolerance of the Materials

SPSS.19 and Excel are used for data analysis, and the cold tolerance of the materials is comprehensively evaluated by a fuzzy membership function method, where a membership function formula is: Uij=(Xij−Xjmin)/(Xjmax−Xjmin); if the physiological indexes of the cold tolerance are negatively related to the cold tolerance, an inverse function is used for conversion, where inverse function value=1−(Xij−Xjmin)/(Xjmax−Xjmin); comprehensive indexes of the cold tolerance:

$$Ui = \sum_{j=1}^{n} Uij/n,$$

where i is an i-th material of all the materials to be tested, j is a j-th physiological index of the cold tolerance of all measured indexes, Xij is a measured value of a j-th physiological index of the i-th material, Xjmin and Xjmax are a minimum measured value and a maximum measured value of j-th indexes of all the materials to be tested respectively, Ui is a comprehensive index of the cold tolerance of the i-th material, and n is a number of the measured physiological indexes of the cold tolerance. When comprehensive indexes of the cold tolerance is larger, the cold tolerance of the materials are better; materials with comprehensive indexes of the cold tolerance larger than or equal to a comprehensive index of the variety 93114 as the cold tolerance control have strong cold tolerance, materials with comprehensive indexes smaller than or equal to a comprehensive index of the Reyan 73397 as the sensitive control have low cold tolerance, and materials with comprehensive indexes between the comprehensive index of the variety 93114 as the cold tolerance control and the comprehensive index of the Reyan 73397 as the sensitive control have medium cold tolerance.

5. Results and Analysis

According to the above-mentioned method for measuring the physiological indexes of the cold tolerance, the leaves of each of the plants are taken for measuring the electrical conductivities before the low temperature treatment, the relative electrical conductivities of all the materials are calculated according to the corresponding formulas in the above-mentioned method, and the obtained relative electrical conductivities are used as control values at the normal temperature to calculate the injury rates of the plants after the low temperature treatment. The values of the relative electrical conductivities are shown in Table 1. After the low temperature treatment for 72 h, the physiological indexes of the cold tolerance are measured according to the above-mentioned method for measuring the physiological indexes of the cold tolerance, and the proline contents, the soluble sugar contents, the malondialdehyde contents, the injury rates, the relative electrical conductivities and the chlorophyll contents are calculated. The relevant data results are shown in Table 2.

TABLE 1

Values of the relative electrical conductivities of the germplasm materials of the *Hevea brasiliensis* before the low temperature treatment

| Material | Relative electrical conductivity |
|---|---|
| MT/C/5 12 | 0.414 |
| RO/PB/1 2 | 0.393 |
| AC/F/6B 40 | 0.415 |
| Reyan 73397 | 0.465 |
| AC/AB/15 54 | 0.420 |
| RO/OP/4 20 | 0.498 |
| RO/CM/11 63 | 0.420 |
| AC/T/1 5 | 0.411 |
| AC/S/10 37 | 0.403 |
| 93114 | 0.474 |
| RO/PB/2 3 | 0.431 |
| Reyan 6 | 0.235 |
| AC/F/6A 36 | 0.357 |
| MT/C/6 11 | 0.464 |
| Reyan 73 | 0.380 |
| Wuxing I3 | 0.349 |

TABLE 2

Values of the physiological indexes of the cold tolerance of the germplasm
materials of the Hevea brasiliensis after the low temperature treatment

| Material | Proline content (µg/mL) | Soluble sugar content (mg/g) | Malondialdehyde content (nmol/g) | Injury rate | Relative electrical conductivity | Chlorophyll content (Color contribution index (CCI)) |
|---|---|---|---|---|---|---|
| Reyan 73 | 60.512 | 11.406 | 18.363 | 0.663 | 0.790 | 17.741 |
| RO/OP/4 20 | 67.044 | 10.717 | 22.401 | 0.321 | 0.651 | 14.074 |
| Wuxing I3 | 34.096 | 10.708 | 15.925 | 0.684 | 0.756 | 21.448 |
| Reyan 6 | 118.184 | 6.566 | 19.290 | 0.467 | 0.670 | 21.674 |
| AC/T/1 5 | 58.449 | 11.547 | 15.701 | 0.583 | 0.758 | 17.730 |
| AC/F/6B 40 | 55.993 | 10.663 | 17.245 | 0.396 | 0.643 | 13.593 |
| Reyan 73397 | 64.016 | 10.661 | 19.446 | 0.373 | 0.646 | 21.274 |
| AC/S/10 37 | 81.101 | 10.487 | 21.468 | 0.352 | 0.612 | 22.622 |
| RO/PB/2 3 | 24.236 | 9.764 | 15.422 | 0.234 | 0.588 | 16.104 |
| AC/AB/15 54 | 28.235 | 10.108 | 16.190 | 0.258 | 0.577 | 18.456 |
| RO/PB/1 2 | 89.173 | 9.731 | 20.429 | 0.208 | 0.518 | 14.841 |
| MT/C/6 11 | 77.672 | 11.493 | 16.005 | 0.669 | 0.786 | 34.752 |
| 93114 | 29.896 | 10.426 | 15.861 | 0.116 | 0.528 | 15.722 |
| AC/F/6A 36 | 51.816 | 8.897 | 15.184 | 0.182 | 0.576 | 23.844 |
| MT/C/5 12 | 59.937 | 10.658 | 19.468 | 0.137 | 0.498 | 36.107 |
| RO/CM/11 63 | 81.132 | 8.237 | 15.397 | 0.074 | 0.409 | 30.644 |
| Xjmax | 118.184 | 11.547 | 22.401 | 0.684 | 0.790 | 36.107 |
| Xjmin | 24.236 | 6.566 | 15.184 | 0.074 | 0.409 | 13.593 |

According to the above method for evaluating the cold tolerance, membership function values of the physiological indexes of the cold tolerance of the materials are calculated according to the values of the physiological indexes of the cold tolerance (Table 2) measured after low temperature stress, and finally the comprehensive indexes of the cold tolerance of the germplasm materials of the *Hevea brasiliensis* are calculated to evaluate the cold tolerance of the materials. The results are shown in Table 3. As the malondialdehyde and the injury rates are negatively correlated with the cold tolerance, the comprehensive indexes of the cold tolerance are calculated by the inverse function for the malondialdehyde contents and the injury rates, and the comprehensive indexes of cold tolerance are calculated by membership function for the proline contents, the soluble sugar contents and the chlorophyll contents, and finally the comprehensive indexes of the cold tolerance for all the materials is obtained. Taking RO/OP/4 20 as an example, membership function values and the comprehensive indexes of the cold tolerance of the materials are calculated as follows:

Membership function value of a proline content of RO/OP/4 20

$Uij=(Xij-Xj\min)/(Xj\max-Xj\min)=(67.044-24.236)/(118.184-24.236)=0.456;$

Membership function value of a soluble sugar content of RO/OP/4 20

$Uij=(Xij-Xj\min)/(Xj\max-Xj\min)=(10.717-6.566)/(11.547-6.566)=0.833;$

Inverse function value of a malondialdehyde content of RO/OP/4 20

$1-Uij=1-(Xij-Xj\min)/(Xj\max-Xj\min)=1-(22.401-15.184)/(22.401-15.184)=0.000$

Inverse function value of a relative electrical conductivity of RO/OP/4 20

$Uij=1-(Xij-Xj\min)/(Xj\max-Xj\min)=1-(0.651-0.409)/(0.790-0.409)=0.365$

Inverse function value of an injury rate of RO/OP/4 20

$Uij=1-(Xij-Xj\min)/(Xj\max-Xj\min)=1-(0.321-0.074)/(0.684-0.074)=0.595$

Membership function value of a chlorophyll content of RO/OP/4 20

$Uij=(Xij-Xj\min)/(Xj\max-Xj\min)=(14.074-13.593)/(36.107-13.593)=0.021$

Comprehensive index of cold tolerance of RO/OP/4 20

$$Ui = \sum_{j=1}^{n} Uij/n = (0.456 + 0.833 + 0.000 + 0.595 + 0.365 + 0.021)/6 = 0.378$$

The cold tolerance of the germplasm materials is evaluated according to the calculation results of the comprehensive indexes of the cold tolerance of all the materials. Among the 14 materials to be evaluated, there are 3 materials with strong cold tolerance, 5 materials with medium cold tolerance and 6 materials with low cold tolerance (Table 4), and the comprehensive indexes of cold tolerance of AC/F/6A 36, MT/C/5 12 and RO/CM/11 63 are higher than the comprehensive index of the variety 93114 as the cold tolerance control and show that AC/F/6A 36, MT/C/5 12 and RO/CM/11 63 have the strong cold tolerance.

TABLE 3

Membership function values of the physiological indexes and the comprehensive indexes of the cold tolerance of the germplasm materials of Hevea brasiliensis

| Material | Membership function value of proline content | Membership function value of soluble sugar content | Inverse function value of malondialdehyde content | Inverse function value of injury rate | Inverse function value of relative electrical conductivity | Membership function value of chlorophyll content | Comprehensive index of cold tolerance |
|---|---|---|---|---|---|---|---|
| Reyan 73 | 0.386 | 0.972 | 0.560 | 0.034 | 0.000 | 0.184 | 0.356 |
| RO/OP/4 20 | 0.456 | 0.833 | 0.000 | 0.595 | 0.365 | 0.021 | 0.378 |
| Wuxing I3 | 0.105 | 0.832 | 0.897 | 0.000 | 0.088 | 0.349 | 0.379 |
| Reyan 6 | 1.000 | 0.000 | 0.431 | 0.354 | 0.315 | 0.359 | 0.410 |
| AC/T/1 5 | 0.364 | 1.000 | 0.928 | 0.165 | 0.085 | 0.184 | 0.454 |
| AC/F/6B 40 | 0.338 | 0.823 | 0.714 | 0.471 | 0.386 | 0.000 | 0.455 |
| Reyan 73397 | 0.423 | 0.822 | 0.410 | 0.509 | 0.378 | 0.341 | 0.480 |
| AC/S/10 37 | 0.605 | 0.787 | 0.129 | 0.544 | 0.468 | 0.401 | 0.489 |
| RO/PB/2 3 | 0.000 | 0.642 | 0.967 | 0.737 | 0.531 | 0.112 | 0.498 |
| AC/AB/15 54 | 0.043 | 0.711 | 0.861 | 0.698 | 0.561 | 0.216 | 0.515 |
| RO/PB/1 2 | 0.691 | 0.635 | 0.273 | 0.780 | 0.714 | 0.055 | 0.525 |
| MT/C/6 11 | 0.569 | 0.989 | 0.886 | 0.024 | 0.011 | 0.940 | 0.570 |
| 93114 | 0.060 | 0.775 | 0.906 | 0.931 | 0.688 | 0.095 | 0.576 |
| AC/F/6A 36 | 0.294 | 0.468 | 1.000 | 0.823 | 0.563 | 0.455 | 0.600 |
| MT/C/5 12 | 0.380 | 0.822 | 0.406 | 0.896 | 0.767 | 1.000 | 0.712 |
| RO/CM/11 63 | 0.606 | 0.335 | 0.971 | 1.000 | 1.000 | 0.757 | 0.778 |

TABLE 4

Evaluation of the cold tolerance of the germplasm materials of the Hevea brasiliensis

| Type of cold tolerance | Germplasm material of Hevea brasiliensis |
|---|---|
| Low cold tolerance | Reyan 73, RO/OP/4 20, Wuxing I3, Reyan 6, AC/T/1 5, AC/F/6B 40 |
| Medium cold tolerance | AC/S/10 37, RO/PB/2 3, AC/AB/15 54, RO/PB/1 2, MT/C/6 11 |
| Strong cold tolerance | AC/F/6A 36, MT/C/5 12, RO/CM/11 63 |

It should be understood that the technical schemes of the present application are not limited to the limits of the above specific embodiments, and any technical variations made according to the technical solutions of the present application, without departing from the scope protected by the objective and claims of the present application, fall within the scope of protection of the present application.

What is claimed is:

1. A method for evaluating cold tolerance of *Hevea brasiliensis*, comprising:
   (1) taking different one-year-old germplasm plants of the *Hevea brasiliensis* with second whorls of leaves entering a stable period as materials, firstly culturing at a normal temperature, then treating at a low temperature, and respectively measuring relative electrical conductivities at a stage of the normal temperature and physiological indexes of the cold tolerance at a stage of the low temperature, wherein a variety 93114 is used as a cold tolerance control and a Reyan 73397 is used as a sensitive control; and
   (2) according to changes of the physiological indexes of the cold tolerance in the germplasm plants of the *Hevea brasiliensis*, comprehensively evaluating the cold tolerance of the materials by using a fuzzy membership function method;
   when comprehensive indexes of the cold tolerance are larger, the cold tolerance of the materials is better; materials with the comprehensive indexes of the cold tolerance larger than or equal to the variety 93114 as the cold tolerance control are evaluated as strong cold tolerance, materials with the comprehensive indexes smaller than or equal to the Reyan 73397 as the sensitive control are evaluated as low cold tolerance, and materials with the comprehensive indexes between two control varieties are evaluated as medium cold tolerance;
   the treating at the low temperature specifically comprises: culturing the different germplasm plants of the *Hevea brasiliensis* to be tested at a normal temperature of 26° C. for 48 h, and treating at 0° C. for 72 h, where a humidity is kept at 90% and a photoperiod comprises 16 h of daylight/8 h of darkness; and
   the physiological indexes of the cold tolerance comprise chlorophyll contents, soluble sugar contents, malondialdehyde contents, proline contents, the relative electrical conductivities and injury rates.

2. The method for evaluating according to claim 1, wherein a membership function formula is $U_{ij}=(X_{ij}-X_{jmin})/(X_{jmax}-X_{jmin})$; wherein an inverse function is used for conversion, if the physiological indexes of the cold tolerance are negatively related to the cold tolerance; an inverse function value $=1-(X_{ij}-X_{jmin})/(X_{jmax}-X_{jmin})$; and the comprehensive indexes of the cold tolerance:

$$Ui = \sum_{j=1}^{n} U_{ij}/n,$$

wherein i is an i-th material of all the materials to be tested, j is a j-th physiological index of the cold tolerance of all measured indexes, $X_{ij}$ is a measured value of a j-th index of the i-th material, $X_{jmin}$ and $X_{jmax}$ are a minimum measured value and a maximum measured value of j-th indexes of all the materials to be tested respectively, $Ui$ is a comprehensive index of the cold tolerance of the i-th material, and n is a number of the physiological indexes of the cold tolerance measured.

3. An application of the method according to claim 1 in genetic breeding of *Hevea brasiliensis*.

* * * * *